United States Patent [19]

Harris

[11] 4,060,689

[45] Nov. 29, 1977

[54] VINYLBENZYL ESTERS OF N-BOC-AMINO ACIDS

[75] Inventor: Nicholas D. Harris, Norwich, N.Y.

[73] Assignee: Morton-Norwich Products, Inc., Norwich, N.Y.

[21] Appl. No.: 751,721

[22] Filed: Dec. 17, 1976

Related U.S. Application Data

[62] Division of Ser. No. 659,967, Feb. 20, 1976.

[51] Int. Cl.² .................... C07C 125/06; A61K 37/02
[52] U.S. Cl. .................................. 560/29; 260/78 A; 260/112.5 R; 424/1 FF; 560/15 F
[58] Field of Search ..................................... 260/471 C

[56] References Cited

U.S. PATENT DOCUMENTS

| | | |
|---|---|---|
| 3,896,105 | 7/1975 | Chai et al. ..................... 260/112.5 R |
| 3,917,580 | 11/1975 | Bumpus et al. ................ 260/112.5 R |
| 3,925,345 | 12/1975 | Bumpus et al. ..................... 424/177 |

OTHER PUBLICATIONS

Zeiger et al., J.A.C.S., 95:3, pp. 880–886, (1973).

Primary Examiner—James O. Thomas, Jr.
Assistant Examiner—G. T. Breitenstein
Attorney, Agent, or Firm—Anthony J. Franze

[57] ABSTRACT

There is described herein the preparation of vinylbenzyl esters of N-BOC amino acids which upon polymerization with styrene and divinylbenzene provide insoluble polymers useful as starting materials for the solid phase synthesis of peptides.

1 Claim, No Drawings

VINYLBENZYL ESTERS OF N-BOC-AMINO ACIDS

This is a division of application Ser. No. 659,967, Feb. 20, 1976.

This invention is concerned with vinylbenzyl esters of N-BOC amino acids representable by the formula:

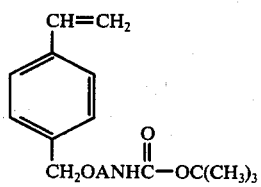

wherein A is the acyl portion of an amino acid.

These esters are useful intermediates in the preparation of peptides. Upon polymerization with styrene and divinylbenzene in the presence of benzoyl peroxide there is formed a solid support susceptible of use in the formation of peptides through the removal of the N-BOC (N-tertiary butyloxy carbonyl) group from the amino acid residue freeing the amino group for reaction with another N-blocked amino acid to introduce a chain of amino acids of whatever desired length to form peptides. The sequence of steps performed upon the vinylbenzyl esters of N-BOC amino acids in polymer form is in accord with the well known Merrifield synthesis of peptides (C&EN Aug. 2, 1971). A distinct advantage in the use of the esters of this invention resides in the avoidance of a chloromethylated polymer employed in conventional peptide syntheses, since the absence of free chloromethyl groups precludes interference with subsequent amino acid coupling as well as methylene bridging. The ester of this invention provide a facile and certain means of obtaining peptides without the opportunity of unwanted side reactions.

The preparation of the vinylbenzyl esters of N-BOC amino acids is readily carried out.

EXAMPLE I

Vinylbenzyl ester of N-BOC-L-alanine

A mixture of 6.4 g (0.034 moles) of N-BOC-L-alanine, 1.8 g (0.017 moles) of sodium carbonate, 5.3 g (0.034 moles) of vinylbenzyl chloride, and 150 ml of dimethyl formamide was stirred at room temperature for 90 hours.

The 150 ml of water was added to the slurry and an oil which precipitated was extracted with benzene. The benzene extract was washed with water, dried with anhydrous sodium sulfate and distilled under vacuum. A 78% yield (8.1 g) of product was collected at 160° C/0.15 mm., $[\alpha]_D^{20} - 36.0°$ (C=1.1, McOH)

Calc. for $C_{17}H_{23}NO_4$: C, 66.86; H, 7.59; N, 4.59, Found: C, 67.12; H, 7.51; N, 4.60.

EXAMPLE II

In a similar fashion according to Example I but using N-BOC-glycine instead of N-Boc-L-alanine and purification by chromatography on silica gel instead of distillation, the vinylbenzyl ester of N-Boc-glycine is produced.

Calc. for $C_{16}H_{21}NO_4$: C, 65.95; H, 7.27; N, 4.80, Found: C, 65.38; H, 7.20; N, 4.52.

EXAMPLE III

As in Example I but using N-Boc-L-leucine instead of N-Boc-glycine there is obtained the vinylbenzyl ester of N-Boc-L-leucine, $[\alpha]_D^{20} - 10.2°$ (C=0.9, CHCl₃).

Calc. for $C_{20}H_{29}NO_4$: C, 69.13; H, 8.4; N, 4.03, Found: C, 69.50; H, 8.67; N, 3.59.

EXAMPLE IV

As in Example I but using N-Boc-O-benzyl-L-tyrosine instead of N-Boc-L-alanine, a solid vinylbenzyl ester of N-Boc-O-benzyl-L-tyrosine was obtained after evaporation of the benzene extracts. Recrystallization from ethanol-water (5:2) gave a white solid, m.p. 68°-70° C, $[\alpha]_D^{20} - 10.8°$ (C=1, AcOH).

Calc. for $C_{30}H_{32}NO_5$: C, 74.05; H, 6.62; N, 2.88, Found: C, 73.70; H, 6.85; N, 2.72.

EXAMPLE V

As in Example I using N-Boc-L-isoleucine instead of N-Boc-glycine there is obtained the vinylbenzyl ester of N-Boc-L-isoleucine $[\alpha]_D^{20} - 1.4$ (C=2, CHCl₃).

Calc. for $C_{20}H_{29}NO_4$: C, 69.13; H, 8.40; N, 3.92, Found: C, 68.55; H, 8.26; N, 3.92.

EXAMPLE VI

As in Example I but using N-Boc-O-benzyl-L-threonine instead of N-Boc-glycine there is obtained the vinylbenzyl ester of N-Boc-O-benzyl-L-threonine, $[\alpha]_D^{20} - 26.3$ (C=1.5, CHCl₃).

Calc. for $C_{25}H_{30}NO_5$: C, 60.73; H, 7.12; N, 3.30, Found: C, 70.20; H, 7.33; N, 3.20.

The vinylbenzyl esters of N-Boc amino acids are readily reacted with styrene and vinylbenzene in the presence of benzoyl peroxide to yield solid polymers as illustrated in the following examples:

EXAMPLE VII

Styrene (71.7 g), vinylbenzyl ester of N-t-butyloxycarbonyl-L-alanine (16.5 g), divinylbenzene (55%, 3.6 g), and benzoyl peroxide (0.83 g) were added to distilled water (110 ml) containing poly vinyl alcohol (2.2 g) and stirred at 70° ± 5° for five hours and at 100° for one and a half hours (blanketed with nitrogen).

The reaction mixture was filtered and the polymer beads washed and dried.

Analysis, after cleavage of the N-Boc group, showed 0.62 moles of alanine per gram of resin.

EXAMPLE VIII

Copolymer of the vinylbenzyl ester of N-Boc glycine, styrene and divinylbenzene

A solution of the vinylbenzyl ester of N-Boc glycine (4.4 g), styrene (19.8 g), divinylbenzene (1 g), and benzoyl peroxide (0.5 g) was added to water (30 ml) containing poly(vinylalcohol) (0.7 g). The mixture was stirred and heated at 65°-70° for five hours and at 100° for one and a half hours (blanketed with nitrogen).

The polymer beads were filtered, washed with water, alcohol, acetic acid, water, and methanol and dried in a vacuum desiccator (21.3 g).

Analysis for glycine gave a value of 0.5 meq. glycine per gram of resin.

EXAMPLE IX

Copolymer of the vinylbenzyl ester of
N-BOC-L-leucine, styrene and divinylbenzene A solution of the vinylbenzyl ester of N-BOC-L-leucine (5 g), styrene (19.8 g), divinylbenzene (1 g) and benzoyl peroxide (0.5 g) was added to water (30 ml) containing poly(vinylalcohol) (0.7 g). The mixture was heated and stirred at 65°–70° for five hours and at 100° for one and a half hours (blanketed with nitrogen).

The polymer beads were filtered, washed with water, alcohol, acetic acid, water, and methanol and dried in a vacuum desiccator (18.2 g).

Analysis for L-leucine showed 0.42 meq. of L-leucine per gram of resin.

EXAMPLE X

Copolymer of the vinylbenzyl ester of
N-BOC-O-benzyl-L-tyrosine, styrene, and divinylbenzene A solution of N-BOC-O-benzyl-L-tyrosine (7 g), styrene (13.2 g), divinylbenzene (0.67 g) and benzoyl peroxide (0.33 g) was added to a well stirred, heated solution of poly vinyl alcohol (0.47 g) in water (20 ml).

The mixture was stirred and heated at 67°–70° five hours and at 100° for one hour. The polymer beads were filtered, washed with water, alcohol, acetic acid, 1 percent sodium hydroxide, water and methanol, and dried in a vacuum desiccator (20.3 g). Analysis for O-benzyl-L-tyrosine gave 0.74 meq. of O-benzyl-L-tyrosine per gram of resin.

EXAMPLE XI

A solution of 10.4 g of styrene, 0.52 g of divinylbenzene, 2.8 g of the vinylbenzyl ester of N-Boc-L-isoleucine, and 0.3 g of benzoyl peroxide was added to a well-stirred, heated solution of 0.35 g of poly(vinyl alcohol) in 20 ml of water.

The mixture was stirred and heated at 65°–70° C for five hours and at 100° C for one hour. The polymer beads were filtered, washed with water, alcohol, acetic acid, water, and methanol, and dried in a vacuum desiccator (11 g).

Analysis for L-isoleucine gave 0.8 meq. of L-isoleucine per gram of resin.

EXAMPLE XII

A solution of 10.4 g of styrene, 0.80 g of divinylbenzene, 3.7 g of the vinylbenzyl ester of O-benzyl-N-Boc-L-threonine, and 0.5 g of benzoyl peroxide were added to a well-stirred, heated solution of 0.3 g of poly(vinyl alcohol) in 40 ml of distilled water.

The mixture was stirred and heated at 65°–70° C. for five hours and at 100° for 1½ hours. The polymer beads were filtered, washed with water, alcohol, acetic acid, water, and methanol, and dried in a vacuum desiccator (11 g).

Analysis for O-benzyl-L-threonine gave 0.9 meq of O-benzyl-L-threonine per gram of resin.

The copolymers as described herein are readily adaptable to the preparation of peptides such as hepta- and octa peptides useful as angiotensin inhibitors (U.S. Pat. No. 3,886,134) using conventional methods of peptide synthesis involvng the buildng of a linear chain of amino acids through repetitive amide linkages employing in such sequential alignment the necessary protective groups susceptible of ready removal by conventional cleavage methods.

What is claimed is:

1. The vinylbenzyl ester of N-tertiarybutyloxy carbonyl-O-benzyl-L-threonine.

* * * * *